US009151750B2

(12) United States Patent
Boehm et al.

(10) Patent No.: US 9,151,750 B2
(45) Date of Patent: Oct. 6, 2015

(54) METHOD FOR CARRYING OUT REACTIONS IN AN ANALYTICAL DEVICE

(75) Inventors: Christoph Boehm, Viernheim (DE); Brigitte Niederberger, Olten (CH); Rijk Edwin Oosterbroek, Cham (CH); Susanne Wuerl, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 288 days.

(21) Appl. No.: 13/410,336

(22) Filed: Mar. 2, 2012

(65) Prior Publication Data
US 2013/0004964 A1 Jan. 3, 2013

Related U.S. Application Data

(63) Continuation of application No. PCT/EP2010/063477, filed on Sep. 14, 2010.

(30) Foreign Application Priority Data

Sep. 21, 2009 (EP) .................................... 09170833

(51) Int. Cl.
*B01L 3/00* (2006.01)
*G01N 33/543* (2006.01)
*G01N 35/00* (2006.01)

(52) U.S. Cl.
CPC .... *G01N 33/54366* (2013.01); *B01L 3/502753* (2013.01); *G01N 35/00069* (2013.01); *B01L 2200/0631* (2013.01);
(Continued)

(58) Field of Classification Search
CPC .................. B01L 3/502753; G01N 33/54366
See application file for complete search history.

(56) References Cited

U.S. PATENT DOCUMENTS 3,825,175 A * 7/1974 Sartory ........................... 494/27
5,622,819 A * 4/1997 Herman ........................... 435/4
(Continued)

FOREIGN PATENT DOCUMENTS

EP 1901054 A2 3/2008
WO 94/27698 A2 12/1994
(Continued)

OTHER PUBLICATIONS

International Search Report issued Oct. 27, 2010 in PCT Application No. PCT/EP2010/063477, 4 pages.
(Continued)

*Primary Examiner* — Melanie Y Brown
(74) *Attorney, Agent, or Firm* — Roche Diagnostics Operations, Inc.

(57) ABSTRACT

Method and system for carrying out heterogeneous chemical or biological reactions are disclosed. The method comprising providing an analytical device having at least one liquid processing unit having at least one reaction chamber and a first inlet channel in fluid communication with the reaction chamber. The method further comprises supplying to the reaction chamber via the first inlet channel or a second inlet channel analyte capturing particles, supplying to the reaction chamber via the first inlet channel or the second inlet channel a liquid sample containing an analyte of interest, and confining by an equilibrium of forces the analyte capturing particles in a particle rearrangement zone within the reaction chamber. The forces comprise a drag force Fd generated by flowing liquids and a counter-oriented force Fg. The method also comprises capturing analytes present in the liquid sample with the particles in the particle rearrangement zone.

17 Claims, 6 Drawing Sheets

(52) U.S. Cl.
CPC ... *B01L 2300/0806* (2013.01); *B01L 2300/087* (2013.01); *B01L 2300/0887* (2013.01); *B01L 2400/0409* (2013.01)

(56) References Cited

U.S. PATENT DOCUMENTS

| | | | |
|---|---|---|---|
| 6,739,456 B2 * | 5/2004 | Svoronos et al. | 209/725 |
| 7,776,267 B2 * | 8/2010 | Lee et al. | 422/72 |
| 2002/0177572 A1 * | 11/2002 | Feldmann et al. | 514/44 |
| 2005/0042768 A1 * | 2/2005 | Fredrick | 436/174 |
| 2006/0073082 A1 | 4/2006 | Ducree et al. | |
| 2006/0086675 A1 * | 4/2006 | E. Purdum | 210/787 |
| 2007/0189910 A1 | 8/2007 | Haeberle et al. | |
| 2008/0073546 A1 * | 3/2008 | Andersson et al. | 250/396 ML |
| 2010/0184020 A1 * | 7/2010 | Beer | 435/6 |

FOREIGN PATENT DOCUMENTS

| | | |
|---|---|---|
| WO | 96/33023 A1 | 10/1996 |
| WO | 98/50163 A1 | 11/1998 |
| WO | 01/68257 A1 | 9/2001 |
| WO | 2004/029221 A2 | 4/2004 |
| WO | 2007/050619 A1 | 5/2007 |
| WO | 2007/106013 A1 | 9/2007 |
| WO | 2007/106579 A2 | 9/2007 |
| WO | 2009/003985 A1 | 1/2009 |

OTHER PUBLICATIONS

Lutz, S. et al., "Unidirectional shake-mode for mixing highly wetting fluids on centrifugal platforms," The proceedings of mTAS 2008 conference, Oct. 12, 2008, pp. 748-750, retrieved from the Internet.

* cited by examiner

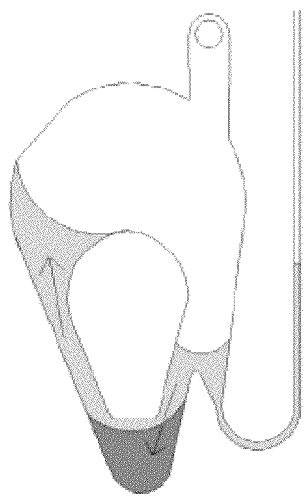  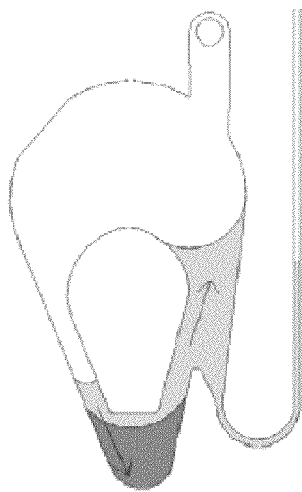
Fig. 8a					Fig. 8b

METHOD FOR CARRYING OUT REACTIONS IN AN ANALYTICAL DEVICE

CROSS-REFERENCE TO RELATED APPLICATIONS

This application is a continuation of PCT/EP2010/063477, filed Sep. 14, 2010, which is based on and claims priority to EP 09170833.9, filed Sep. 21, 2009, which is hereby incorporated by reference.

BACKGROUND

The present disclosure generally relates to in-vitro diagnostics and, in particular, to a method for carrying out heterogeneous chemical or biological reactions involving the use of analyte capturing particles.

In the field of in-vitro diagnostics, there is a need for the automated heterogeneous assay of chemical and biological samples. Due to several advantages such as, for example, low sample and reagent requirement, the possibility to integrate several assay steps into a single device, increased reaction kinetics, fast analysis times and hence high throughput, many efforts have been made to develop microfluidic systems in recent years.

Packed bed columns, built up as a pile of beads, have been commonly used, for example, in chromatography in chemical analysis for decades. Also in diagnostic applications, the use of porous frit structures is known in the art. For example, immunoassays on a rotating disc, where liquids flow through a packed bed column driven by centrifugal force, have been disclosed. Different ways of building columns with beads, or particles, in miniaturized systems are also known. A conventional way is to use slurries from which a fixed structure is obtained. Typically, a bead-liquid emulsion, or suspension, is flown through, along or over a chamber in which the beads are trapped. This trap can be either a small passage, such as a shallow slit, a porous material like a fleece or filter, for example, a sintered porous material, or larger beads. Another method is to trap the particles in a magnetic field. Typically, these methods all have the particles trapped in a forward flow direction in common. This means that the flow-resistance is fixed or increased when liquid is flown through. Due to an increased packing grade while trapping the particles, the column flow resistance will increase, possibly leading to clogging. When the column is used to bind molecules flowing through, this clogging effect can be more severe. In the case where the beads are trapped in a field, like for instance magnetic, the drag forces may exceed the trapping forces on the beads, resulting in bead loss. When single particles are packed in a geometrical way via a narrowed passage, the obtained pore-size depends on the bead-size. Because larger particles may not provide sufficient binding capacity, smaller particles are preferred but they will yield smaller pores and thus a higher flow resistance. As a consequence, there is a practical limitation of what bead-size can be used for a given flow pressure range. This can be a problem when, for instance, using centrifugation for driving the flow as the obtainable pressures are small. Once a column is clogged, it may be very difficult to recover it.

SUMMARY

According to the present disclosure, methods of carrying out heterogeneous chemical or biological reactions involving the use of analyte capturing particles which enables efficient capturing of analytes while avoiding high flow resistance and the risk of clogging is disclosed. This can be achieved by confining the analyte capturing particles in a particle rearrangement zone, in which, due to equilibrium of forces, the particles are able to rearrange themselves but from which the particles are unable to escape In accordance with one embodiment of the present disclosure, mixing with reagents can be more efficient thus increasing the kinetics of reaction and reducing further the time of the assay as well as the consumption of samples and reagents.

In accordance with another embodiment of the present disclosure, the analytical device can be generic, simple and cost efficient, wherein the particles can be introduced in the form of a reagent at the moment of the assay without the need to pre-pack a particle column in advance or during manufacturing.

In accordance with yet another embodiment of the present disclosure, the particles can be applied, as a suspension for example, directly into the reaction chamber of the analytical device and dried therein during the manufacturing of the analytical device. One advantage of this embodiment is that the particles can be already present in the analytical device and will be resuspended by a liquid, by the sample itself for example, automatically during test performance without additional steps of reagent admixture. Moreover various types and sizes of particles can be used which can enormously increase the flexibility of the assay and the device Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 8a and b illustrate the principle of fluidic movements caused by Euler forces according to the shake-mode variant according to an embodiment of the present disclosure.

DETAILED DESCRIPTION

Figure 1:
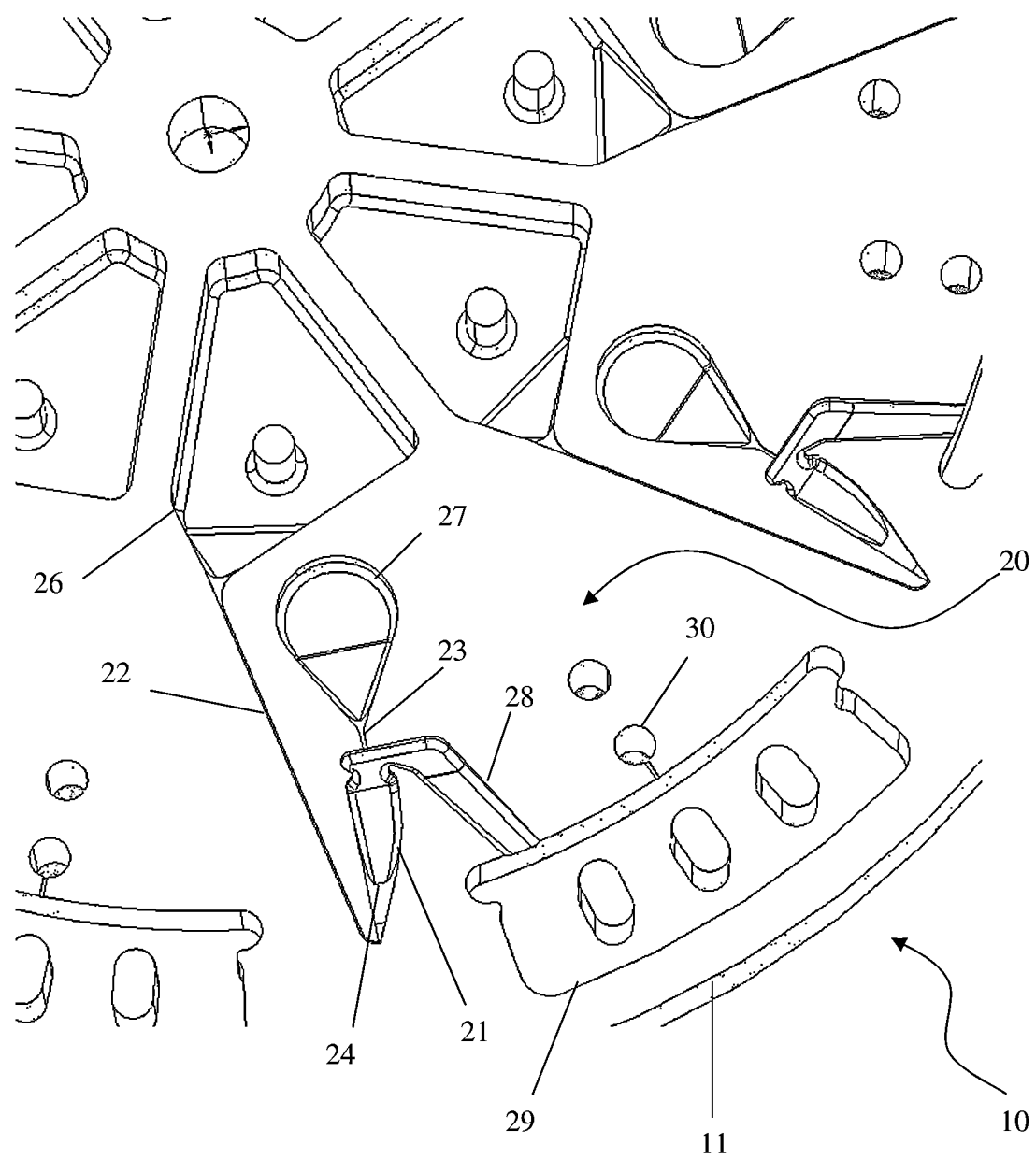
FIG. 1 illustrates a partial perspective top view of an exemplary analytical device showing the elements of a possible liquid processing unit according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The analytical device according to the present disclosure may be used in chemistry like in in-vitro diagnostics and can be adapted to carry out various assay operations comprising mixing liquids as well as detecting analytes contained in liquid samples. It may be, for example, used for diagnostic assays like for example clinical chemistry assays and immunoassays. Typical diagnostic assays include, for example, the qualitative and/or quantitative analysis of analytes such as albumin, ALP, Alanine Aminotransferase, Ammonia, Amylase, Aspartat Aminotransferase, Bicarbonate, Bilirubin, Calcium, Cardiac Markers, Cholesterol, Creatinine Kinase, D-Dimer, Ethanol, g-Glutamyltransferase, Glucose, HBA1c, HDL-Cholesterol, Iron, Lactate, Lactate Dehydrogenase, LDL-Cholesterol, Lipase, Magnesium, Phosphorus inorganic, Potassium, Sodium, Total Protein, Triglycerides, UREA, Uric Acid or any other suitable diagnostic assay.

The recited liquids may be samples and reagents. Samples are liquid solutions in which one or more analytes of interest can be potentially found. Samples may comprise chemical analytes, for example, organic chemicals, and the analytical device can be adapted to carry out one or more chemical assays, for example, a drug interaction screening, an environmental analysis, the identification of organic substances, synthesis, or any other suitable chemical assay Samples can be also biological as for example, body fluids like blood, serum, urine, milk, saliva, cerebrospinal fluid, or any other body fluid and may comprise chemical as well as biological analytes, such as nucleic acids, proteins, peptides, lipids, metabolites, or any other biological analyte.

The term reagent is used to indicate any liquid, for example, a solvent or chemical solution, which can be mixed with a sample and/or other reagent in order, for example, for a reaction to occur, or to enable detection. A reagent can be for example another sample interacting with a first sample. A reagent can be also a diluting liquid, it may comprise an organic solvent, a detergent, or it may be a buffer or a solution for performing washing steps. A reagent in the more strict sense of the term may be a liquid solution containing a reactant, typically a compound or agent capable for example of binding to or transforming one or more analytes present in a sample, eventually producing a detectable result. Examples of reactants are enzymes, enzyme substrates, conjugated dyes, protein-binding molecules, nucleic acid binding molecules, antibodies, chelating agents, promoters, inhibitors, epitopes, antigens, catalysts, or any other suitable reactant. Optionally dry reagents may be present in the analytical device and be dissolved by a sample, another reagent or a diluting liquid.

Typically, reagents are mixed with samples and the assay is a heterogeneous reaction making use of a solid support. The solid support can comprise of particles susceptible to a force such as a drag force and a field force and which can remain corpuscular, that is, are suspendable but not dissolvable in the liquid they come in contact with. The particles are typically analyte capturing particles, wherein the term capturing indicates the ability of the particles, directly or indirectly, for example via a surface coating, to bind or retain at least temporarily at least one analyte contained in the sample and/or to interact in a specific or selective manner with the analytes.

The following are examples of heterogeneous reactions: Heterogeneous immunoassay; Catalysis, where the particles may have a catalytic surface; Capturing and purification of nucleic acids; Capturing of other biological material such as cells or viruses; Affinity chromatography or Chemical solid phase extraction.

These particles can be embodied as suspendable beads, or micro-spheres, with a diameter for example in the micrometer range. In one embodiment, the diameter can be between about 0.1 and about 20 micrometer. In another embodiment, the diameter can be between about 1 and about 5 micrometer. In applications requiring a high sensitivity, the use of smaller particles can be preferred, because such smaller particles comprise a higher surface-to-volume ratio which can be beneficial for a higher sensitivity of an assay. In alternative embodiments, particles of different density and different analyte capturing properties can be applied into the reaction chamber. The use of analyte capturing particles with different densities and different analyte capturing properties can allow a simultaneous detection of multiple analytes by their respective analyte capturing particles, because the different analyte capturing particles can be sorted according to their densities in different zones of the detection compartment (for example by centrifugal forces). Also, by size, shape and density, the drag and field forces on the beads can be "tuned" or tailor-made to the specific needs. By surface roughness and porosity, the surface-to-volume-ratio can be adapted. Commercially available beads such as latex beads or magnetic beads provided with immobilized reactants, or with binding elements to which reactants can be immobilized, are examples of suitable particles.

In some embodiments, the use of transparent particles can be beneficial because the use of at least partially transparent particles allows an optical detection also in depth (i.e., in all three spatial dimensions) because the upper particle layers of a packed particle bed will not shadow the layers below. This can result in an increased signal intensity and increased sensitivity.

The analyte capturing particles can be supplied to the analytical device in the form of a liquid reagent, for example, a liquid suspension, or can already be provided in the reaction chamber, such as by an analyte capturing particles pre-loading during manufacturing of the analytical device and can be resuspended by a liquid, such as by the sample itself, automatically during test performance without additional steps of reagent admixture.

The analytical device can have a device body comprising at least one liquid processing unit. According to one embodiment, the device body can be a carrier comprising one or more liquid processing units. The device body and the liquid processing units may be separate entities joined with each other at the moment of use. In this case, the device body could be made of a rigid material such as, for example, metal, glass or ceramics, or a plastic material such as, for example injection molded, and can have features such as for example compartments to receive liquid, processing units, alignment pins and/or holes, clamps, levers, or screws to fix the liquid processing units. The device body may have holes enabling optical detection or may be transparent.

According to one embodiment, the device body and the at least one liquid processing unit form one integral piece, made of, for example, a plastic material, for example, injection molded. The device body can be at least partially transparent. According to one embodiment, the device body can be disposable. The device body can have a disc-like shape. In one embodiment, the disc-like shape can be round, for example, with the footprint of a compact disc (CD).

The liquid processing unit can be either a separate element that can be coupled to the device body or can be an integral part of the device body, comprising interconnected microfluidic structures by which it can be possible to achieve miniaturization and integration of the various assay operations. The term integral is used herein to indicate that the liquid processing unit can be at least partially built in the device body at the moment of production and is not separable from the device body.

The liquid processing unit can comprise at least two layers, one substrate layer and one cover layer. The microfluidic structures can be created, in one embodiment, on the upper surface of the substrate and can be sealed from the top with the cover layer. According to one embodiment, the substrate layer can be the device body. According to another embodiment, the substrate layer can be a separate element that can be coupled to the device body. The cover layer can be made of the same material as the substrate layer or of a different material such as, for example, a thin polymeric foil, that can be transparent in one embodiment. One way of achieving sealing between the substrate layer and the cover layer can be to use bonding technologies, such as thermal bonding, gluing, injection molding, for example, two-component injection molding or any other suitable bonding method. The sealing, in one embodiment, can occur at the moment of production. It may however occur before use. Terms like upper and top are used herein as relative and not absolute. The position of substrate layer and cover layer can be, for example, reversed. The cover layer can comprise, in one embodiment, holes or access ports to enable the access of liquids such as samples, reagents and/or air to the microfluidic structures.

A plurality of liquid processing units can be symmetrically arranged around a central axis of rotation of the device body. The liquid processing unit can comprise at least one reaction chamber, for mixing at least one liquid with analyte capturing particles. The reaction chamber can be a microfluidic structure defined as a cavity in or between the substrate layer and the cover layer, defining a lower wall and upper wall respectively, and delimited by side walls. The volume of the reaction chamber can define the maximum volume of reaction mixture. The volume can be in the microliter and milliliter range, for example about 1 microliter up to several milliliters, typically below about 1 mL. The liquid processing unit can further comprise at least one inlet channel in fluid communication with the reaction chamber for delivering at least one liquid to the reaction chamber. The liquid processing unit can comprise at least one inlet chamber in fluid communication with the reaction chamber via at least a first inlet channel. Different liquid processing units may be partially interconnected between them, for example, one access port or inlet channel might be in common to more than one liquid processing unit.

At least a part of the reaction chamber can be designed as a particle rearrangement zone that is a zone in which the particles are able to rearrange themselves, but from which the particles are unable to escape, at least temporarily. In the embodiment of a flow-through variant, the particle rearrangement zone can be defined by equilibrium of forces. The forces can comprise a drag force generated by liquids flowing through the first inlet channel and a counter-oriented force. Particles may escape the particle rearrangement zone or may stop rearranging themselves if the equilibrium between the two types of forces is lost, for example, if one type of force is reduced or increased compared to the other or one is removed.

A drag force is a hydrodynamic force dependent on flow velocity generated by liquid flowing, for example, by a liquid flowing into the reaction chamber via said at least one first inlet channel and acting on the particles suspended in the liquid in the direction of the liquid flow relative to the particles. Drag forces can also be induced by Euler forces (which can be induced by accelerations of the analytical device) in combination with appropriate chamber designs (see shake-mode variant below). A counter-oriented force can be a force acting on the analyte capturing particles induced by a gravitational field, a magnetic field, an electromagnetic field, an electrostatic field, an acceleration field comprising centrifugal, translational, rotational acceleration fields or any other suitable field. In other words, the drag force and the counter-oriented force can be opposite to each other. As the liquid flow tends to drag particles in the flow direction, the field-induced force tends to move the particles in the opposite direction against the liquid flow.

By regulating the field-induced force and/or the liquid flow velocity, the boundaries of the particle rearrangement zone can be varied. For example, if the field-induced force is increased and the drag force is decreased, the particle rearrangement zone can become smaller, that is the particles are less dispersed and rearrange themselves only in a limited volume or part of the reaction chamber. If the drag force is stopped, the particles may eventually sediment, or agglomerate, with very little or no rearrangement occurring any longer. This situation may occur temporarily, for example, before a new liquid addition and it may be preferred at the end of the reaction when detection is eventually performed, because such an agglomeration of the particles results in an increased signal intensity and sensitivity. If, on the contrary, the counter-oriented force is decreased and the drag force increased, the particle rearrangement zone can become larger, that is the particles are more dispersed and rearrange themselves in a larger volume or part of the reaction chamber. If the counter-oriented force is further decreased, the particles may eventually be dragged out of the reaction chamber. So, by regulating drag and counter-oriented forces the effective particle concentration, diffusion distances and flow resistance can be determined and adjusted.

In an alternative embodiment to the flow-through embodiment described above, the shake-mode embodiment, the arrangement of the particles can be achieved by the interaction of a field force with a counter-orientated drag force which can be induced by Euler forces. The use of Euler forces in microfluidic structures is well-known and used in different embodiments, most preferably for mixing purposes in a shake. Euler forces can result from an acceleration of the analytical device and can have effects on both the suspended particles and particularly on the liquid in the reaction chamber. Euler forces can be occurring in a direction perpendicular to the field force (centrifugal force). Depending on the geometric design of the reaction chamber, the resulting fluid flows can occur also in other directions because the walls of the reaction chamber can deflect the originally perpendicular flow into different directions.

Caused by the alternating acceleration of the analytical device (for example, by a see-saw movement of the analytical device) and the alternating Euler forces, a liquid flow can be induced which flows alternating from one side of the reaction chamber to the other side of the reaction chamber and which can flow through the particle arrangement at each change of acceleration of the analytical device. Compared to the alternative embodiment of a flow-through embodiment, a shake-mode embodiment can also cause a kind of pump functionality which can move a liquid multiple times through a particle arrangement. Therefore, all the advantages and options described in connection with the flow-through embodiment can also be applicable for the shake-mode embodiment.

If the analytical device is designed as a centrifugal test device, the field force can be generated by a fast rotational movement, preferably with a constant velocity. In this embodiment, the field force can be the centrifugal force. The counter-oriented drag forces induced by Euler forces can be generated by rapid changes of the rotation direction (shake-mode). For the shake-mode, the particles can have, in one embodiment, a density which is slightly larger than the density of the surrounding liquid (for example, the sample). This can allow both a sedimentation and agglomeration of the particles for detection purposes (which can increase the signal intensity and sensitivity) and also for an improved resuspension of the particles in the shake-mode embodiment.

The "pumping" of the liquid through the particle arrangement can occur, in one embodiment, in a shake-mode with low final rotational velocities and high rotational accelerations. This can result in large Euler forces (resulting in large drag forces) in combination with a loosened particle arrangement and therefore in an optimized flow-through of the liquid relative to the particle arrangement which increases the binding efficiency.

By using the shake-mode embodiment, the field force can be a centrifugal force which varies strongly from about zero at the beginning of the acceleration (zero rotational speed) to maximum at the end of the acceleration phase (maximum rotational speed). This can mean that initially the beads can get dragged with the flow but once the centrifugal force becomes larger than the drag forces at higher rotational speeds, the bead, and also the fluid, can flow backwards thereby confining the beads in a capturing zone and leveling the fluids at both sides of the capturing zone. (The capturing zone can be located at the part of the reaction chamber which is most distant from the rotational axis. The capturing zone can be located within the connecting section.) Since the beads can have a larger density than the fluid, they can be stronger influenced by the centrifugal forces than the fluid. Hence the beads can be more confined to the capturing zone than the fluid, resulting in a bed of beds that is flown through in alternating directions by the fluid. By defining the rotational accelerations and speed profiles, the effect of the pumping action due to Euler forces and bead-capturing due to centrifugal forces can be controlled. For the agglomeration of the particles, for example, for detection purposes, a high and constant rotational force can be preferred. This can result in no Euler, but high centrifugal, forces forcing the beads (which can have a higher density than the liquid) to agglomerate on the side of the reaction chamber most distant from the rotation axis.

With both embodiments, the flow-through and the shake mode, and due to the above mentioned methods for loosening and agglomerating the particles, an efficient mass transport (resulting in an improved binding and washing efficiency) can be combined with a agglomerated and compact arrangement of the particles for detection (resulting in increased signal intensity and sensitivity).

For efficient reactions and/or efficient washing, i.e., fast reaction kinetics and low volume consumption, it can be advantageous that the analyte capturing particles rearrange themselves. In the particle rearrangement zone, the particles are in continuous movement, i.e., they continuously change position within the liquid, thus resulting in improved mixing. This can mean higher chance and shorter time for the particles to find an analyte to capture, for the bound analytes or reagents to find a reactant in the liquid solution and for the bound-free reagents to be more easily washed away after the reaction, while using smaller volumes.

In defining the boundaries of the particle rearrangement zone, the geometry of the reaction chamber may play an important role. According to a flow-through embodiment, the reaction chamber, at least in correspondence of the particle rearrangement zone, can have a tapered or funnel structure with diverging walls in the flow direction. This geometry can gradually reduce the downstream directional flow velocity of liquids flowing in the reaction chamber via the first inlet channel. The first inlet channel can be fluidically connected to the narrower edge or corner of the tapered structure or bottom side of the funnel. As the width of the reaction chamber increases, the flow velocity and hence the drag force acting on the particles can decrease until the drag force is outbalanced by the counter-oriented force preventing the particles from moving further downstream. The method may therefore comprise reducing the directional flow velocity of liquids entering the reaction chamber via the first inlet channel by designing the reaction chamber with a tapered shape.

The method may comprise splitting liquids flowing through the reaction chamber into multiple streams. This can have the effect of improving the flow profile, e.g. to flatten the flow profile, which normally tends to be parabolic, or to have the particles more distributed in the center of the reaction chamber and less on the outer walls. According to one embodiment, the method may comprise dividing the reaction chamber into a serially arranged set of diffuser-like compartments. Diffuser-like compartments in series may be used to trap a fraction, for example, size dependent, or a part of the particles, and/or be used for different reaction steps.

Also, the flow velocity can be controlled by varying the size of the inlet channel and/or designing the inlet channel with a flow resistor, for example, a restriction of the cross-section, inducing hydraulic resistance to the flow and thus reducing the flow velocity. The method may thus comprise controlling the flow velocity of liquids through the first channel via a flow resistor.

In one embodiment, the entire reaction chamber, or at least the part being filled with liquid, can be a particle rearrangement zone so that the particles can be distributed throughout the liquid. Typically, the particle rearrangement zone occupies less than 50% of the volume of the reaction chamber in order to stay within safety margins in case of drag or counter-oriented force fluctuations.

According to a shake-mode embodiment, the reaction chamber can be divided by a central element into two sub-chambers which are connected by a connecting section that connects the two sub-chambers at their ends distant from a rotational axis. The central element can work as a barrier and can cause a flow of liquid through the connecting section from one sub-chamber into the other sub-chamber in the shake-mode. During the shake-mode, the liquid can be alternately "pumped" from one sub-chamber into the other sub-chamber. Also the particles can be arranged in the connecting section (and optionally also in the adjacent parts of the respective sub-chambers) due to their higher density. The pumping movement forced by the Euler forces in the shake-mode can cause a multiple flow-through of the liquid through the particle arrangement in this section. These multiple liquid movements relative to the particles can result in an increased binding efficiency of the analyte molecules within the liquid to their respective binding partners which can be immobilized onto the surfaces of the particles.

Like the flow-through embodiments, the sub-chambers of shake-mode embodiments can have a geometric structure with diverging walls in a flow direction directed to the rotational axis. In one embodiment, this tapering in direction to the connecting section can occur in all spatial directions, i.e., also the height of the reagent chamber can decrease in the direction to the rotational axis-distant connecting section. Because this connecting section can be the most distant part of the reaction chamber in relation to the rotational axis, an agglomeration of the particles by centrifugal forces can occur in this section. This agglomeration of particles by centrifugal forces can be supported by this geometric design of the reaction chamber because the decrease of the geometric dimensions towards this part of the reaction chamber can cause additional capillary forces which can be beneficial to keep the particles in this part of the reaction chamber, even at relatively low rotational speeds. Altogether, such a geometric design can be beneficial for an agglomeration of the particles in this part of the reaction chamber and therefore, in one embodiment, this connecting section (and optionally the adjacent parts of the respective sub-chambers) can be also used as a detection chamber in which the optical signal of the agglomerated particles can be detected.

The reaction chamber may comprise one or more inlet channels (e.g. for sample fluids, liquid reagents or washing solutions). In one embodiment, these inlet channels can be located on the opposite side of the reaction chamber in relation to the connecting section, i.e., close to the rotational axis. The reaction chamber may comprise also one (or more) outlet channels. In one shake-mode embodiment, the outlet channel can be located slightly above the particle arrangement zone. This can allow an almost entire exchange or removal of liquids within this zone without a loss of particles resulting in very efficient.

In one embodiment, the outlet channel can be designed in form of a microfluidic siphon comprising valving functionalities and can allow a control of the chamber emptying process by preventing the emptying of the reaction chamber during the shake-mode process. The geometric design of such microfluidic siphons is known in the art.

According to one embodiment, the liquid processing unit can have at least two inlet channels in fluid communication with the reaction chamber. The second inlet channel can be used, for example, to introduce at least the particles and the first channel can be used to introduce other liquids, which upon entering the reaction chamber can exercise a drag force on the particles introduced via the second channel. This may prevent, for example, clogging of the first inlet channel especially if the cross-section is small or if it comprises a flow resistor.

In an alternative embodiment, the particles can be applied, as a suspension, for example, directly into the reaction chamber of the analytical device and dried therein during the manufacturing of the analytical device. For these purposes, the reagent chamber may comprise, in one embodiment, recesses which can allow a controlled and defined application and drying of particles or also other reagents directly into the reaction chamber.

According to one embodiment, the liquid processing unit can comprise at least one outlet channel. The liquid processing unit may further comprise at least one waste chamber in fluid communication with the reaction chamber via the at least one outlet channel for receiving liquids flowing out of the reaction chamber. The waste chamber can typically be larger than the reaction chamber in order to accommodate volumes of liquids which sequentially and/or continuously flow through the reaction chamber. The method may thus comprise inducing liquids to flow out of the reaction chamber into a waste chamber in fluid communication with the reaction chamber via an outlet channel, while the particles are retained in the reaction chamber. One waste chamber may receive liquid from more reaction chambers from the same or different liquid processing units.

The liquid processing unit may further comprise a liquid dosing chamber for delivering a defined volume of liquid, for example, a sample, to the reaction chamber. A liquid dosing chamber can be a microfluidic structure defined as a cavity in or between the substrate layer and the cover layer, the volume of which can define the volume of liquid to be used in the assay once it has been filled. This volume can typically be below about 1 microliter, for example, about 200 nanoliters. The liquid dosing chamber can have, in one embodiment, an elongated shape and can have at least two microchannels connected to it: a third liquid inlet channel allowing liquid to fill the liquid dosing chamber; and one liquid decanting channel defining where the liquid dosing chamber starts and the liquid inlet channel ends and allowing excess liquid to be guided to a waste chamber. At about the opposite side, the sample dosing chamber can comprise a microfluidic valve such as, for example, a geometric or hydrophobic valve based on changes of the geometrical surface characteristics and surface energy. One way of realizing a geometric valve can be by a restricted conduit ending blunt at the inner edge of a larger channel or chamber. Maintaining the driving force, typically a counter-oriented force, below that required to break the energy barrier of the valve can cause the liquid to stop at this position and any excess to be deviated to the decanting channel characterized by having barrier energy lower than that of the valve. The method may thus comprise dosing defined volumes of liquids to be delivered to the reaction chamber via at least one liquid dosing chamber in fluid communication with the reaction chamber via at least said first inlet channel. Bypass channels in fluid communication with the first inlet channel may be used to introduce other liquids, including for example diluting liquids.

According to one embodiment, the reaction chamber may also serve as detection chamber. This means that the presence and/or quantization of captured analytes can be determined directly in the reaction chamber after or during the mixing between liquids and the analyte capturing particles. Detection can typically be optical detection, for example, based on photometric methods such as absorbance measurement, turbidimetry, luminescence, bioluminescence, chemiluminescence, fluorescence, phosphorescence or any other suitable method. Therefore, according to one embodiment, the reaction chamber, at least partially, can be made of a transparent material enabling optical detection in the reaction chamber.

The method can be automated, for example, carried out at least in part by an automatic analytical instrument which can be part of an analytical system.

According to one embodiment, an analytical instrument can comprise a rotatable supporting device and the analytical device can be placed onto the rotatable supporting device so as to be able to rotate therewith. The analytical instrument may further comprise a pipetting unit for supplying liquids to a reaction chamber via at least one inlet channel. The analytical instrument may further comprise a detection unit, for example, an optical unit for detecting the result of the reactions.

The rotatable supporting device may be comprised of, for example, plastic or metal such as aluminum and may have a disk-like shape and can be rotated around a rotational axis driven by means of an actuator such as an electric motor.

The pipetting unit may comprise a reusable washable needle, for example, a steel needle, or disposable pipette tips. Typically, the pipetting unit can be operatively coupled to an automated positioning device for moving the pipette tip or needle with respect to the analytical device and, for example, may be mounted to a transfer head that can be moved in two directions of travel in a plane, for example, by guiding rails and a third direction of travel orthogonal to the plane, for example, by a spindle drive.

The detection unit may comprise a light source such as, for example, a xenon lamp, a laser, or LEDs, the optics, for example, mirrors, lenses, optical filters, fiber optics, for guiding and filtering the light, one or more reference channels, a CCD sensor or the like. The detection unit can for example be adapted for detecting analytes captured by the analyte capturing particles. For example, it may be embodied as a fluorescence detector for detecting fluorescence light emitted from fluorescence markers made to be bound to analytes captured by the analyte capturing particles.

The analytical system may further comprise a controller for controlling the automated analysis of samples according to a predetermined process operation plan which, e.g., may be embodied as programmable logic controller running a computer-readable program provided with instructions to perform operations in accordance with the process operation plan.

The analytical system may further comprise a reagent rack for receiving reagent containers, a sample rack for receiving sample containers, a washing station for washing for example, the pipetting needle, a shaker or mixing paddle for suspending analyte capturing particles contained in liquid reagent containers, and the like.

Supplying liquids to the reaction chamber via the at least one inlet channel can be carried out automatically by means of a pipetting unit as described with reference to the analytical instrument.

Detection of the signal generated by the signal generating analytes can be carried out by an optical detection unit as described with reference to the analytical system and may be based on photometric methods chosen from absorbance measurement, turbidimetry, luminescence, bioluminescence, chemiluminescence, fluorescence, phosphorescence and the like.

Since temperature may play an important role for chemical and biological reactions, the method may comprise heating and/or cooling at least the reaction chamber, wherein heating and cooling can generally mean providing heat to or subtracting heat from the reaction chamber. This can comprise maintaining the liquid contained in the reaction chamber at a constant temperature and/or subjecting the liquid to temperature changes, for example temperature gradients, repeated temperature cycles, and the like.

Different ways of heating and cooling are possible. This may be achieved for instance by means of temperature regulating units, for example, Joule heating elements, infrared heating elements or Peltier elements, in contact with the reaction chamber, or by means of air streams. The all analytical device may be contained in a tempered housing of the system, for example.

Referring initially to FIG. 1, FIG. 1 shows an analytical device 10 for heterogeneous chemical or biological reactions comprising a device body 11 with a disc-like shape. The device body 11 can comprise a plurality of liquid processing units 20. The liquid processing unit 20 can comprise a reaction chamber 21 for mixing at least one liquid with analyte capturing particles and two inlet channels 22, 23. A first inlet 22 and a second inlet channel 23 can be in fluid communication with the reaction chamber 21 for delivering liquids to the reaction chamber 21.

The liquid processing unit 20 can further comprise a first inlet chamber 26 in fluid communication with the reaction chamber 21 via the first inlet channel 22 and a second inlet chamber 27 in fluid communication with the reaction chamber 21 via the second inlet channel 23. The liquid processing unit 20 can also comprise an outlet channel 28 and one waste chamber 29 in fluid communication with the reaction chamber 21 via the outlet channel 28 for receiving liquids flowing out of the reaction chamber 21. A vent 30 in fluid communication with the waste chamber 29 can allow air to escape as liquids flow into the reaction chamber 21 and eventually into the waste chamber 29.

The analyte capturing particles can be introduced into the reaction chamber 21 via the second inlet channel 23 after pipetting a volume of liquid suspension into the second inlet chamber 27. Other liquids can be introduced into the reaction chamber 21 via the first inlet channel 22 after pipetting respective volumes into the first inlet chamber 26.

The device body 10 can be made of an injection-molded polymer and can be covered by a thin foil (not shown) sealing the liquid processing units 20. Access ports or holes can be provided in correspondence of the inlet chambers 26, 27 and vent 30 in order to allow liquids to be introduced and air to escape.

The reaction chamber 21 can be designed as a particle rearrangement zone 24, in which, due to an equilibrium of forces, particles 12 can be able to rearrange themselves but from which the particles 12 are unable to escape. The forces can comprise a drag force Fd generated by liquids flowing through the first inlet channel 22 and a counter-oriented force Fg. This principle is illustrated schematically in FIGS. 2 and 3. The counter-oriented force Fg can be a centrifugal force, i.e., an acceleration force, generated by rotating the analytical device 10. The drag force Fd can be dependent on centrifugal force as well as liquids flow into the reaction chamber 21 from the inlet chamber 26 during rotation of the analytical device 10. The average flow velocity of the liquids in the reaction chamber can however be dependent also on the dimensions of the first inlet channel 22 and the geometry of the reaction chamber 21.

Particularly, the average flow velocity can be made to gradually decrease from the bottom (zone A in FIG. 3) to the top (zone C in FIG. 3) of the reaction chamber 21. This can be achieved for example by designing the reaction chamber 21 with a tapered shape, in this case with diverging walls in the flow direction, from A towards C in FIG. 3. As the flow velocity decreases also the drag force Fd acting on the particles 12 decreases. Although, parallel walls could be used as well, having diverging walls can allow for larger particle rearrangement zones 24 and can reduce the risks that particles 12 escape from the reaction chamber 21 via the outlet channel 28. While liquids may overflow out of the reaction chamber 21 via the outlet channel 28, the particles 12 remain, dynamically rearranging themselves, in the particle rearrangement zone 24 while liquids flow through the first inlet channel 22 and can be compacted at the bottom of the reaction chamber 21 when liquids stop flowing through the first inlet channel 22. For limiting the maximum flow velocity and better controlling the equilibrium of forces, a narrow and long first inlet channel 22, or the presence of a flow resistor 31, can be used. This can also have the effect to prolong the reaction time while the slow supply of fresh liquids, for example reagents, makes reactions more efficient, i.e. by shifting the reaction equilibrium towards product formation. The counter-oriented force Fg acting on the particles 12 can determine how far the particles 12 move into direction of zone C, which is how large the particle rearrangement zone 24 is. If the force Fg increases, the particle rearrangement zone 24 will be small and located at the bottom of the reaction chamber 21. If the force Fg decreases, the particles 12 will be more distributed, i.e. the particles rearrangement zone 24 will occupy most of or all the reaction chamber 21. Thus varying the geometry of the reaction chamber 21 and the first inlet channel 22 and adjusting the rotational speed of the analytical device 10, the point (zone B in FIG. 3) at which the forces Fd and Fg acting on the particles 12 in the reaction chamber 21 reach an equilibrium varies and so does the size and location of the particle rearrangement zone 24. In zone C, Fg can overcome Fd and any particle 12 entering that zone tends to return towards B. In zone A, Fd can overcome Fg and any particle 12 in that zone tends to move towards B. As a result, the particles 12 can rearrange themselves and can be trapped in the particle rearrangement zone 24 until both forces Fd and Fg are maintained.

Figure 2:
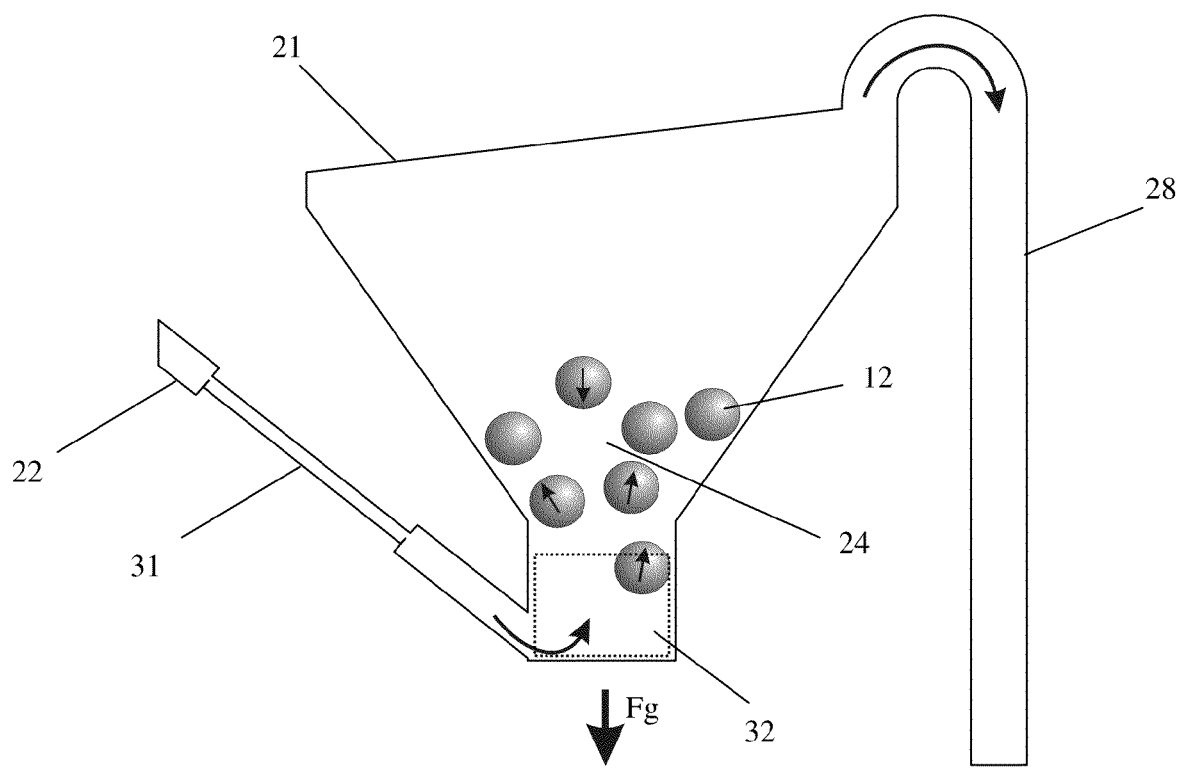
FIG. 2 illustrates schematically one embodiment of reaction chamber according to a flow-through embodiment of the present disclosure.
Figure 3:
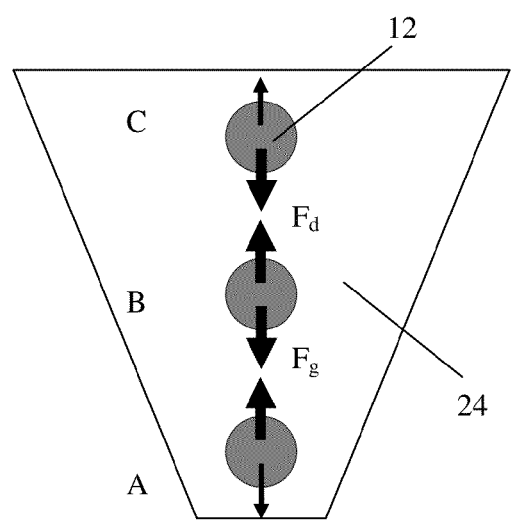
FIG. 3 illustrates the principle of confining the analyte capturing particles in a particle rearrangement zone according to an embodiment of the present disclosure.

The reaction chamber 21 may have different shapes and opening-angles that can influence the flow-velocity profile in different ways. Beside one diverging shape, multiple diffuser-like compartments organized in parallel or in series may be implemented. The ideal geometry can create a decreasing velocity gradient in flow-direction only and a constant uniform velocity in the orthogonal direction. However in practice, a parabolic flow-profile is very likely to occur. The suspended particles 12 might get collected, e.g. accumulate or form aggregates, in low-velocity zones, such as in correspondence of stepped or sharply diverging walls. This unwanted effect may be promoted by rough or electrostatically charged surfaces. Therefore, rather steep and fluent contours are preferred, eventually with structures promoting a uniform flow profile. The geometry may be designed such that the suspended material can be collected at the end of a reaction in a dedicated area 32 of the reaction chamber 21 for example detection purposes as shown in FIG. 2.

Figure 4:
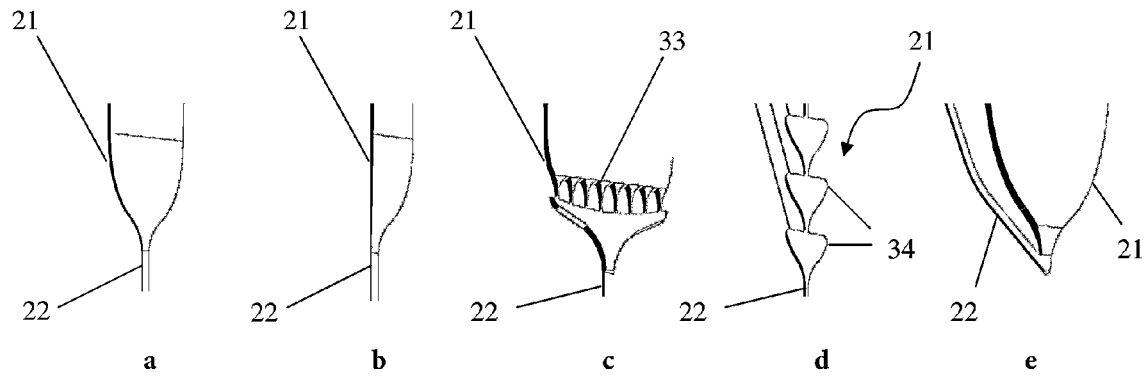
FIG. 4 illustrates schematically additional embodiments of reaction chambers according to an embodiment of the present disclosure.

In FIG. 4 other examples of reaction chamber 21 designed to function at least in part as particle rearrangement zone 24 are schematically shown. In FIG. 4a, a symmetrically diverging reaction chamber 21 is shown. In FIG. 4b, an asymmetrically diverging reaction chamber 21 is shown. In FIG. 4c, the reaction chamber 21 comprises a structure 33 to split the flow into many parallel streams that is like having multiple parallel rearrangement zones is illustrated. This structure can provide a more uniform flow profile by flattening the flow profile and can cause the particles 12 to be more distributed in the center of the reaction chamber 21 and less on the outer walls. In FIG. 4d, diffuser-like compartments 34 in series where each compartment 34 traps a fraction, for example size dependent, or a part of the particle 12 is shown. FIG. 4e is simply a variant of FIG. 4a wherein the position of the inlet channel 22 can vary and is similar to the embodiment shown in FIGS. 1 and 2. In other embodiments, filters (not shown) could also be used.

Figure 5:
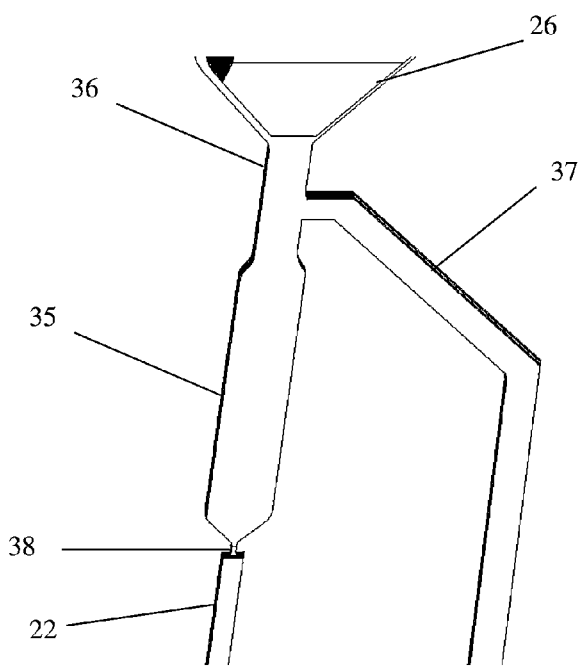
FIG. 5 illustrates an embodiment comprising a dosing chamber according to an embodiment of the present disclosure.

FIG. 5 shows the structure of an exemplary dosing chamber 35 in fluid communication with the reaction chamber 21 via the first inlet channel 22, for delivering a defined volume of liquid, for example a sample, to the reaction chamber 21. The volume defined by the liquid dosing chambers 35 can be about 200 nanoliters. The liquid dosing chamber 35 can have an elongated shape and three microchannels connected to it: a third liquid inlet channel 36 in fluid communication with the first inlet chamber 26 (not shown in FIG. 5) allowing liquid to fill the liquid dosing chamber; a liquid decanting channel 37 defining where the liquid dosing chamber 35 starts and the third liquid inlet channel 36 ends and allowing excess liquid to be guided to a waste chamber (not shown); and the first inlet channel 22 in fluid communication with the reaction chamber 21. At the interface between the dosing chamber 35 and the sample dosing chamber 22, a geometric valve 38 can be located. At this position, the sample flow can temporarily stop and any excess of sample can be deviated to the decanting channel 37. Afterwards the driving force, in this case the centrifugal force, can be increased above that required to break the energy barrier of the valve 38 and approximately 200 nanoliters of liquid sample can be transferred to the reaction chamber 21 via the first inlet channel 22.

Figure 6:
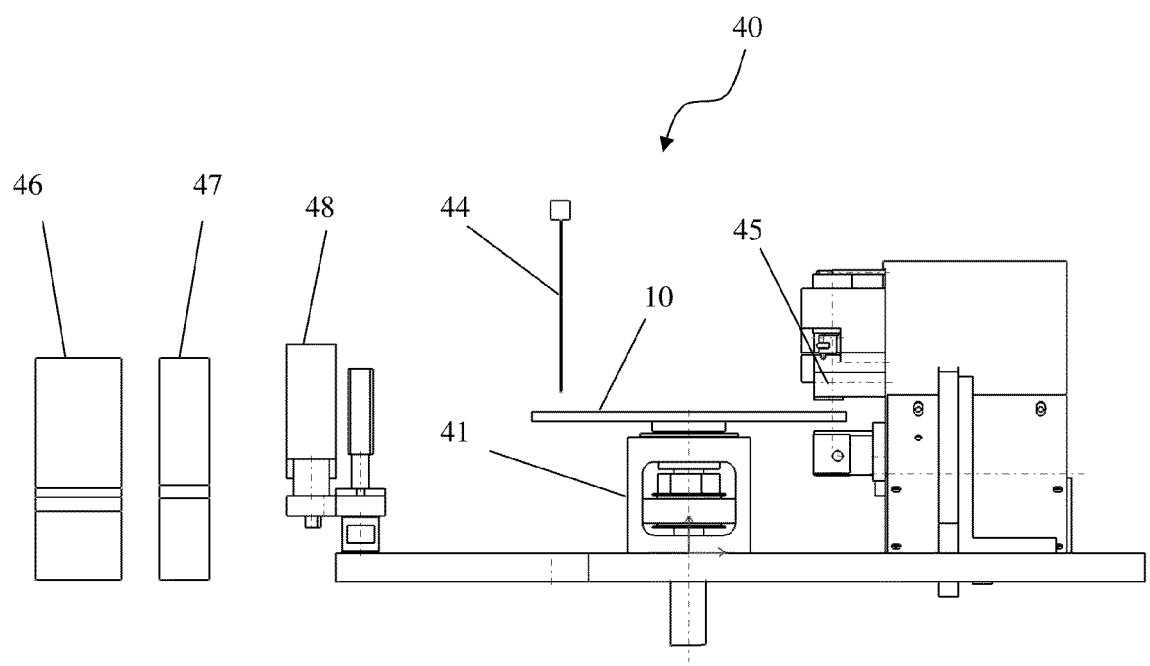
FIG. 6 illustrates schematically an analytical system comprising an analytical device such as that shown in FIG. 1 according to an embodiment of the present disclosure.

FIG. 6 shows schematically an analytical system 40 for heterogeneous chemical or biological reactions comprising an instrument. The instrument can comprise a rotatable supporting device 41. An analytical device 10 as that of FIG. 1 can be removably fixed to the supporting device 41 so as to rotate therewith. The instrument can further comprise a needle 44, part of a pipetting unit (not shown), for supplying liquids to the reaction chambers 21 via the inlet channels 22,23, an optical unit 45 for detecting the result of the reactions, a reagent rack 46 for receiving reagent containers, a sample rack 47 for receiving sample containers, and a washing unit 48 for washing the needle 44 of the pipetting unit.

Figure 7:
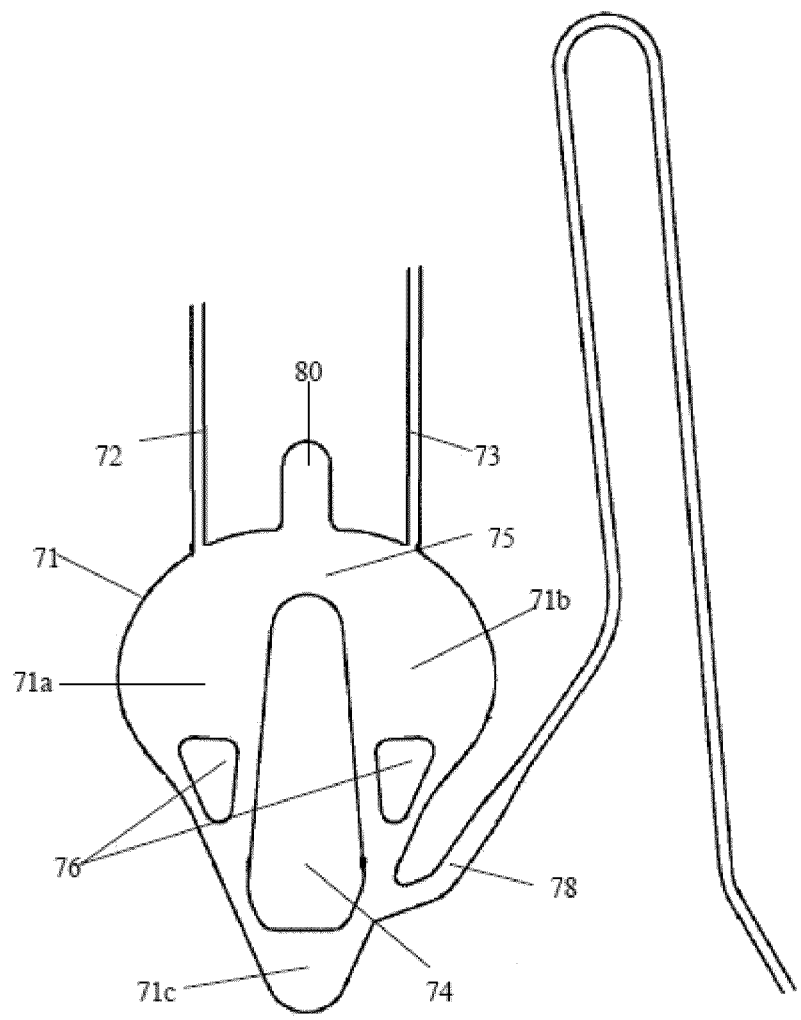
FIG. 7 illustrates schematically an embodiment of reaction chamber according to a shake-mode embodiment of the present disclosure.

FIG. 7 shows schematically one embodiment of reaction chamber according the shake-mode embodiment. The reaction chamber 71 can be divided into two sub-chambers 71a and 71b connected by a connecting section 71c located on the side of the reagent chamber 71 most distant from the rotational axis. This partition of the reaction chamber 71 into two sub-chambers 71a and 71b can be by a solid and raised structure 74. This solid structure 74 can provoke the flow of liquid between the two sub-chambers 71a and 71b to be directed into the connecting section 71c. In addition to the connecting section 71c on the side of the reaction chamber 71 that is more distant from the rotational axis, an additional connection 75 between the sub-chambers 71a and 71b can be on the side of the reaction chamber 71 closer the rotational axis. This additional connection 75 can be used as a volume compensation area when fluids are transported between the two sub-chambers 71a and 71b in the shake-mode. In the embodiment of FIG. 7, the rotational axis can be located above the shown fluidic structure.

A first inlet channel 72 and a second inlet channel 73 can be in fluid communication with the reaction chamber 71. These inlet channels 72 and 73 can be used for the application of liquids into the reaction chamber, for example, for the application of reagent liquids or washing liquids. Also an outlet channel 78 can be in fluid communication with the reaction chamber 71 for receiving liquids flowing out of the reaction chamber 71. This outlet channel 78 can, in one embodiment, be in fluid communication with a waste chamber (not shown) which can receive and stores all liquids used in the reagent chamber 71. In one embodiment, the outlet channel 78 can be designed as a microfluidic siphon (see FIG. 7).

In FIG. 7, a vent 80 in fluid communication with the reaction chamber 71 can allow air to escape as liquids flow into the reaction chamber 71.

Recesses 76 are also shown in FIG. 7. These recesses 76 can be depressions in the bottom wall of the reaction chamber 71 and can be advantageously used for a defined application of reagents and also particles into the reaction chamber 71 during manufacturing of the analytical device. In one embodiment, liquid reagents or particle suspensions can be provided and dried into these recesses 76 during manufacturing of the analytical device. During use of the analytical device 10, the reagents or particles can be solubilised or resuspended by contact with liquids (for example, the sample or buffer solutions) which can save an additional reagent application step during use of the analytical device 10.

The analyte capturing particles can either be introduced into the reaction chamber 71 via the inlet channel 72, 73 or can be already present. In one embodiment, they can be dried into the recesses 76 and can be resuspended by a liquid entering the reaction chamber 71 via the inlet channel 72, 73. In alternative embodiments, the analyte capturing particles can be provided at different sites within the reaction 71, for example in the connecting section 71c. In one embodiment, the particles can have a higher density than the surrounding liquid. As a result of this higher density, the particles can be agglomerated at the section of the reaction chamber 71 which is most distant from the rotational axis when applying centrifugal forces. This can be the connecting section 71c. Therefore, in one embodiment, this connecting section 71c can also be used as the detection area, because within this area the particles can be agglomerated in a high packing density which can be very beneficial for high signal intensity and sensitivity. For these reasons, the connection section 71c can be made of transparent material or can comprise at least an optical window which can allow a signal detection by optical methods.

The other designs embodiments, for example, the geometric features shown in and described in context with FIGS. 1 to 5 can be used analogously for the shake-mode embodiment according to FIG. 7.

FIGS. 8a and 8b show schematically two different states respectively occurring in a reaction chamber very similar to the reaction chamber shown in FIG. 7 during use and application of a shake-mode acceleration profile. The darker area in the lower part of the structure can represent the arrangement of particles located within this connecting section of the reaction chamber and the lighter area above the darker particle area can represent the liquid which can be "pumped" through the particle arrangement in the shake-mode. In addition to the light area, liquid can of course be also present within the dark area, filling the spaces between the particles.

During the shake-mode, Euler forces can appear causing an effective flow of liquid from one sub-chamber to the other sub-chamber. These alternating effective liquid flows through the particle arrangement can result in an improved binding efficiency for analytes onto the binding surfaces of the particles.

The following is an example of method for carrying out heterogeneous chemical or biological reactions. The method comprising:
a) placing an analytical device 10 such as that of FIG. 1 in the instrument of system 40,
b) supplying to the reaction chamber 21 via the second inlet channel 23 analyte capturing particles 12, or providing analyte capturing particles 12 in the reaction chamber 71, by a analyte capturing particles pre-loading during manufacturing of the analytical device,
c) supplying to the reaction chamber 21, 71 via the first inlet channel 22, 72 a liquid sample containing an analyte of interest,
d) confining by an equilibrium of forces the analyte capturing particles 12 in a particle rearrangement zone 24 comprised in the reaction chamber 21, 71, the forces comprising a drag force Fd, generated by the liquid sample flowing through the first inlet channel 22 or induced by Euler forces in a shake-mode, and a counter-oriented centrifugal force Fg generated by rotating the analytical device 10,
e) capturing analytes present in the liquid sample with the analyte capturing particles 12 in the particle rearrangement zone 24 while the liquid sample is flowing.

In the following another more detailed example of method for carrying out heterogeneous chemical or biological reactions according to the invention is given. The method comprising:

a) placing an analytical device 10 such as that of FIG. 1 in the instrument of system 40,
b) supplying by the pipetting unit a liquid suspension comprising analyte capturing particles 12 to the second inlet chambers 27,
c) transferring by rotating the analytical device 10 the first liquid reagent to the reaction chambers 21 via the second inlet channels 23,
d) supplying by a pipetting unit liquid samples to the first inlet chambers 26,
e) transferring by rotating the analytical device 10 the liquid samples to the reaction chambers 21 via the first inlet channels 22,
f) capturing analytes present in the liquid samples by means of the analyte capturing particles 12,
g) supplying by a pipetting unit to the first inlet chambers 26 a first liquid reagent comprising signal generating conjugates for binding to analytes captured by the analyte capturing particles 12,
h) transferring by rotating the analytical device 10 the first reagent to the reaction chambers 21 via the first inlet channels 22,
i) supplying by a pipetting unit to the first inlet chambers 26 a wash buffer for washing out bound-free signal generating conjugates,
j) transferring by rotating the analytical device 10 the wash buffer to the reaction chambers 21 via the first inlet channels 22,
k) repeating steps i) and j) as necessary for sufficient washing to let previous liquids contained in the reaction chambers and excess of washing buffer flow out of the reaction chambers 21 into the waste chambers 29 via the outlet channels 28,
l) confining by an equilibrium of forces at least temporarily during steps c), e), f), h), j) the analyte capturing particles 12 in the particle rearrangement zones 24 comprised in the reaction chamber 21, the forces comprising a drag force Fd generated by liquids flowing through the inlet channels 22 and a counter-oriented centrifugal force Fg,
m) collecting the analyte capturing particles 12 carrying the conjugate-bound analytes in the areas 32 by centrifugal force Fg only,
n) detecting the signal generated by the conjugate-bound analytes captured by the analyte capturing particles 12.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for carrying out heterogeneous chemical or biological reactions, the method comprising:
providing an analytical device comprising at least one liquid processing unit, the at least one liquid processing unit comprising at least one reaction chamber and a first inlet channel in fluid communication with a corner of the at least one reaction chamber;

providing analyte capturing particles in the at least one reaction chamber;

supplying to the at least one reaction chamber via the first inlet channel or a second inlet channel a liquid sample containing an analyte of interest;

confining by an equilibrium of forces and geometry of the at least one reaction chamber and the first inlet channel the analyte capturing particles in a particle rearrangement zone within the at least one reaction chamber, the forces comprising a drag force Fd, generated by liquids flowing through the first inlet channel by centrifugal forces or generated by liquids flowing induced by Euler forces within the reaction chamber, and a counter-oriented force Fg induced by a centrifugal force; and capturing analytes present in the liquid sample with the analyte capturing particles in the particle rearrangement zone.

2. The method according to claim 1, further comprising:
providing to the at least one reaction chamber a first liquid reagent comprising signal generating conjugates for binding to analytes captured by the analyte capturing;
supplying to the at least one reaction chamber via the first inlet channel a second liquid reagent for washing unbound signal generating conjugates out of the particle rearrangement zone; and
detecting a signal generated by the conjugate-bound analytes captured by the analyte capturing particles.

3. The method of claim 1, wherein the analyte capturing particles are provided to the at least one reaction chamber via the first inlet channel or a second inlet channel.

4. The method of claim 1, wherein the analyte capturing particles are provided to the at least one reaction chamber by pre-loading the analyte capturing particles during manufacturing of the analytical device.

5. The method of claim 1, wherein the first liquid reagent is provided to the at least one reaction chamber via the first inlet channel.

6. The method of claim 1, wherein the first liquid reagent is provided to the at least one reaction chamber by pre-loading the first liquid reagent during manufacturing of the analytical device.

7. The method according to claim 1, wherein the at least one reaction chamber has a tapered shape whereby downstream directional flow velocity of liquids flowing in the at least one reaction chamber via the first inlet channel is reduced.

8. The method according to claim 1, wherein the drag force Fd is induced by an Euler force which is generated by acceleration of the analytical device.

9. The method claim 1, further comprising,
splitting liquids flowing through the at least one reaction chamber into multiple streams.

10. The method according to claim 1, further comprising,
dividing the at least one reaction chamber into serial diffuser-like compartments.

11. The method according to claim 1, further comprising,
dosing defined volumes of liquids to be delivered to the at least one reaction chamber via at least one liquid dosing chamber in fluid communication with the at least one reaction chamber via the first inlet channel.

12. The method according to claim 1, further comprising,
inducing liquids to flow out of the at least one reaction chamber into a waste chamber in fluid communication with the at least one reaction chamber via an outlet channel.

13. The method according to claim 1, wherein the first inlet channel comprises a flow resistor for controlling flow velocity of liquids.

14. The method according to claim 1, further comprising,
rotating the analytical device.

15. The method according to claim 1, further comprising,
changing temperature of the at least one reaction chamber.

16. The method according to claim 1, further comprising,
agglomerating the analyte capturing particles by centrifugal forces in a detection area within the at least one reaction chamber most distant from the rotational axis used to generate the centrifugal forces.

17. The method according to claim 2, wherein detecting the signal generated by the conjugate-bound analytes captured by the analyte capturing particles is based on photometric methods of absorbance measurement, turbidimetry, luminescence, bioluminescence, chemiluminescence, fluorescence, phosphorescence or combinations thereof.

* * * * *